(12) United States Patent
Liu

(10) Patent No.: US 10,398,306 B2
(45) Date of Patent: Sep. 3, 2019

(54) OPTICAL IMAGING DEVICE AND METHOD FOR IMAGING A SAMPLE

(71) Applicant: Nanyang Technological University, Singapore (SG)

(72) Inventor: Linbo Liu, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 0 days.

(21) Appl. No.: 14/765,778

(22) PCT Filed: Mar. 3, 2014

(86) PCT No.: PCT/SG2014/000101
§ 371 (c)(1),
(2) Date: Aug. 4, 2015

(87) PCT Pub. No.: WO2014/137290
PCT Pub. Date: Sep. 12, 2014

(65) Prior Publication Data
US 2015/0366451 A1    Dec. 24, 2015

Related U.S. Application Data

(60) Provisional application No. 61/774,340, filed on Mar. 7, 2013.

(51) Int. Cl.
*A61B 3/10* (2006.01)
*G01B 9/02* (2006.01)
(Continued)

(52) U.S. Cl.
CPC ............ *A61B 3/102* (2013.01); *A61B 3/0008* (2013.01); *A61B 3/0025* (2013.01);
(Continued)

(58) Field of Classification Search
CPC .. A61B 3/102; A61B 5/0066; G01B 9/02044; G01B 9/02091
See application file for complete search history.

(56) References Cited

U.S. PATENT DOCUMENTS 5,321,501 A    6/1994 Swanson et al.
6,341,036 B1   1/2002 Tearney et al.
(Continued)

FOREIGN PATENT DOCUMENTS

WO    03/062802 A2    7/2003
WO    2012/035170 A1  3/2012

OTHER PUBLICATIONS

Ling Wang,"Wavelength encoded OCT imaging using swept-source", 2007, SPIE (Year: 2007).*
(Continued)

*Primary Examiner* — Maurice C Smith
(74) *Attorney, Agent, or Firm* — Seed IP Law Group LLP

(57) ABSTRACT

According to embodiments of the present invention, an optical imaging device is provided. The optical imaging device includes an optics arrangement configured to generate an extended-source illumination pattern including a plurality of separate spectral bands, and to illuminate a respective section of a sample to be imaged with a respective spectral band of the plurality of separate spectral bands, wherein the optics arrangement is further configured to form an interference signal from a sample light comprising respective return lights from respective sections of the sample illuminated by respective spectral bands of the extended-source illumination pattern, and a reference light, and a detector configured to receive the interference signal for generating an image corresponding to the sections of the sample. According to further embodiments of the present
(Continued)

invention, a method for imaging a sample and a method for generating an image are also provided.

29 Claims, 11 Drawing Sheets

(51) Int. Cl.
*A61B 3/00* (2006.01)
*A61B 5/00* (2006.01)

(52) U.S. Cl.
CPC .......... *A61B 5/0066* (2013.01); *A61B 5/7257* (2013.01); *G01B 9/02001* (2013.01); *G01B 9/02007* (2013.01); *G01B 9/02034* (2013.01); *G01B 9/02044* (2013.01); *G01B 9/02089* (2013.01); *G01B 9/02091* (2013.01); *A61B 5/0064* (2013.01); *G01B 2290/20* (2013.01)

(56) References Cited

U.S. PATENT DOCUMENTS

| | | | |
|---|---|---|---|
| 6,564,087 B1 | 5/2003 | Pitris et al. | |
| 7,428,057 B2* | 9/2008 | De Lega | G01B 9/023 356/497 |
| 7,551,293 B2* | 6/2009 | Yelin | G01B 11/2441 356/456 |
| 7,796,270 B2* | 9/2010 | Yelin | A61B 5/0066 356/456 |
| 7,872,757 B2 | 1/2011 | de Boer et al. | |
| 7,916,387 B2 | 3/2011 | Schmitt | |
| 8,780,176 B2* | 7/2014 | Yelin | A61B 5/0066 348/42 |
| 9,295,391 B1 | 3/2016 | Tearney et al. | |
| 2004/0036838 A1* | 2/2004 | Podoleanu | A61B 3/102 351/206 |
| 2005/0018201 A1* | 1/2005 | de Boer | A61B 5/0059 356/479 |
| 2005/0128488 A1 | 6/2005 | Yelin et al. | |
| 2005/0254008 A1* | 11/2005 | Ferguson | A61B 3/1025 351/205 |
| 2006/0187462 A1* | 8/2006 | Srinivasan | A61B 3/102 356/479 |
| 2007/0081236 A1* | 4/2007 | Tearney | A61B 5/0062 359/390 |
| 2007/0188855 A1* | 8/2007 | Shishkov | A61B 5/0062 359/362 |
| 2008/0094637 A1* | 4/2008 | de Boer | A61B 5/0059 356/479 |
| 2008/0097225 A1* | 4/2008 | Tearney | A61B 18/22 600/478 |
| 2009/0027689 A1 | 1/2009 | Yun et al. | |
| 2010/0045778 A1* | 2/2010 | Yelin | A61B 5/0066 348/45 |
| 2013/0215431 A1* | 8/2013 | Ellerbee | G01B 9/02091 356/479 |
| 2013/0250290 A1* | 9/2013 | Tkaczyk | A61B 5/0066 356/300 |
| 2013/0265545 A1* | 10/2013 | Buckland | A61B 3/13 351/206 |

OTHER PUBLICATIONS

Chasles et al., "Optimization and characterization of a structured illumination microscope," *Optics Express* 15(24):16130-16140, 2007.
Choma et al., "Sensitivity advantage of swept source and Fourier domain optical coherence tomography," *Optics Express* 11(18): 2183-2189, 2003.
de Boer et al., "Improved signal-to-noise ratio in spectral-domain compared with time-domain optical coherence tomography," *Optics Letters* 28(21): 2067-2069, 2003.
Girard et al., "Shadow Removal and Contrast Enhancement in Optical Coherence Tomography Images of the Human Optic Nerve Head," *Investigative Ophthalmology & Visual Science* 52(10):7738-7748, 2011.
Häusler et al., ""Coherence Radar" and "Spectral Radar"—New Tools for Dermatological Diagnosis," *Journal of Biomedical Optics* 3(1): 21-31, 1998.
Hogg et al., "Quantum-dot diodes provide sources for optical coherence tomography," *SPIE Newsroom*, The International Society for Optical Engineering, 2006, 3 pages.
Huang et al., "Optical coherence tomography," *Science* 254(5035): 1178-1181, 1991.
International Comission on Illumination, "17-42 angular subtense [α]," 2014, retrieved from http://eilv.cie.co.at/term/42, on Sep. 28, 2015.
International Electrotechnical Commission, "Safety of laser products—Part 1: Equipment Classification, requirements and user's guide," IEC 60825-1, Edition 1.2, 2001, 122 pages.
Leitgeb et al., "Performance of fourier domain vs. time domain optical coherence tomography," *Optics Express* 11(8): 889-894, 2003.
Nössig et al., "Largest base of optical coherence technology worldwide with more than 10,000 units installed," Carl Zeiss Meditec Press Releases, Sep. 11, 2008, retrieved from http://www.zeiss.com/corporate/en_de/media-forum/press-releases.html?id=2D4B8A2D1E164576C12574C100317CFB, on Sep. 28, 2015, 2 pages.
Schulmeister et al., "Location and size of the apparent source for laser and optical radiation ocular hazard evaluation," 11th International Congress of the International Radiation Protection Association, Madrid, Spain, May 23-28, 2004, 9 pages.
Swanson et al., "Ophthalmic OCT Reaches $1 Billion Per Year: But Reimbursement Clampdown Clouds Future Innovation," Optical Coherence Tomography News, Jul. 9, 2011, retrieved from http://www.octnews.org/articles/2844561/ophthalmic-oct-reaches-1-billion-per-year-but-reim/, on Sep. 28, 2015, 5 pages.
Wojtkowski et al., "Real-time in vivo imaging by high-speed spectral optical coherence tomography," *Optics Letters* 28(19): 1745-1747, 2003.

* cited by examiner

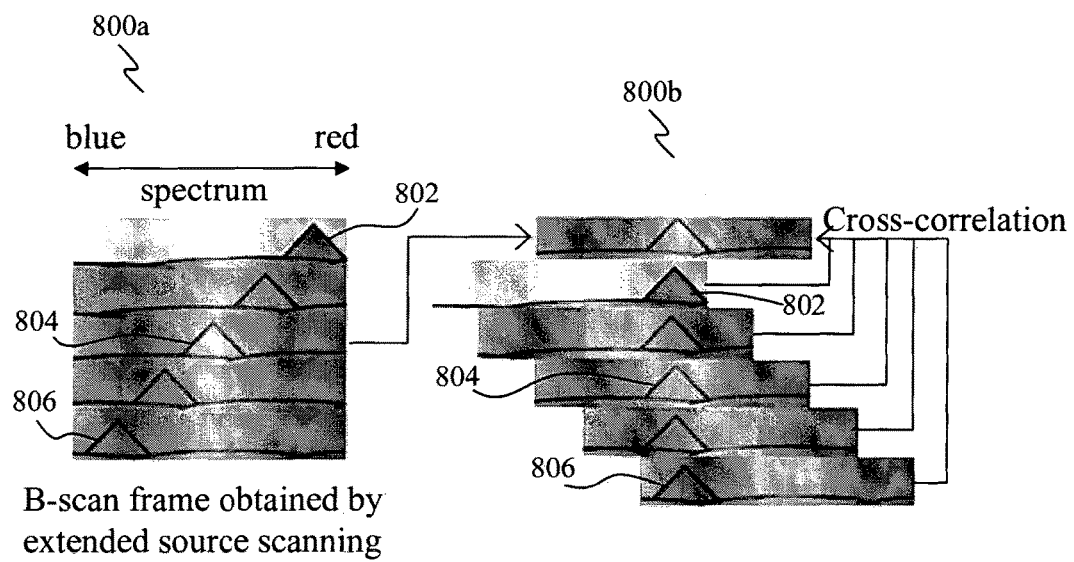
B-scan frame obtained by extended source scanning
FIG. 8A
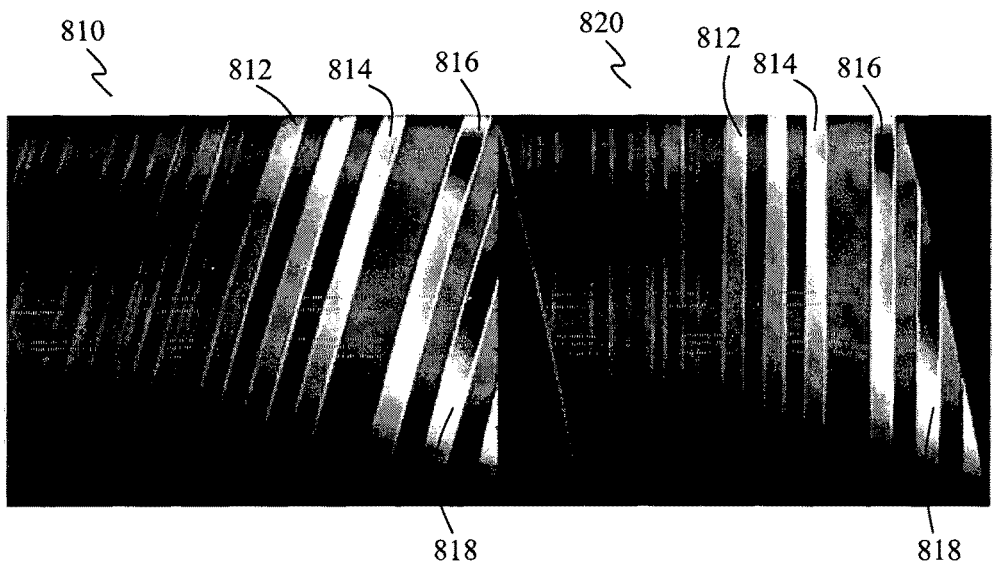
FIG. 8B
FIG. 8C

900

OPTICAL IMAGING DEVICE AND METHOD FOR IMAGING A SAMPLE

CROSS-REFERENCE TO RELATED APPLICATION

This application claims the benefit of priority of US provisional application No. 61/774,340, filed 7 Mar. 2013, the content of it being hereby incorporated by reference in its entirety for all purposes.

TECHNICAL FIELD

Various embodiments relate to an optical imaging device and a method for imaging a sample.

BACKGROUND

Optical coherence tomography (OCT) is an established in vivo optical imaging technology that provides micrometer resolution and millimeter penetration depth in human tissues. It has been validated clinically that OCT enables in vivo visualization of human eyes, coronary arteries, gastrointestinal tracts, and airway tissues at a resolution comparable to histology. OCT has been widely used clinically to diagnose a wide range of diseases in the retina and the anterior segment of the eye. Recently, intracoronary OCT technology has been used clinically to image the coronary artery disease, and endoscopic OCT technology used for detection of gastrointestinal neoplasm.

Ophthalmology is the dominant OCT application. In 2010, the estimated OCT charges in U.S.A and worldwide were $780 M and $1 B respectively, and it is estimated that the sale of ophthalmologic OCT systems was approximately $250 million. There are more than 10 suppliers of ophthalmic OCT products, where one such supplier alone delivered over 10,000 ophthalmic OCT units worth $0.7 B to the market by 2008. Over the next four years, the OCT market is expected to grow annually at approximately 60%.

Since its invention in 1991, OCT technology has evolved from a time-domain OCT (TD-OCT, first generation technology) to a spectral-domain/Fourier-domain OCT (second generation technology). An existing spectral-domain OCT (SD-OCT) setup 100 is illustrated in FIG. 1, showing a small-source SD-OCT setup with a light source (LS) 102. Based on the laser safety regulations provided in IEC (International Electrotechnical Commission) 60825, a "small source" is defined as a source with an angular subtense, $\alpha$, less than, or equal to, the minimum angular subtense, $\alpha_{min}$ (generally defined to be 1.5 mrad). The angular subtense, $\alpha$, may be defined as a visual angle subtended by a source at the eye of an observer or at the point of measurement. The angular subtense, $\alpha$, may also be defined as the angle subtended by an apparent source (defined as the real or virtual object that forms the smallest possible retinal image) as viewed at a point in space, e.g. at the viewer's eye.

In the small-source SD-OCT setup 100, an output light 104 of the light source (LS) 102 is divided by a beam splitter 106 into a sample light radiation 108 and a reference light radiation 110. The sample light radiation 108 propagates through a sample arm (S) 120 of the setup 100 while the reference light radiation 110 propagates through a reference arm (R) 150 of the setup 100, where the sample arm (S) 120 and the reference arm (R) 150 define an interferometer.

The sample light radiation 108 is directed or guided to a tissue sample 190 under investigation through focusing optics, e.g. a collimation lens (L1) 122 and a focusing lens (L2) 124 and one or more beam scanners (SC) 126 in the sample arm (S) 120. The sample light radiation 108 is directed to a spot 192 on the tissue sample 190. A reflected and/or backscattered light radiation 109 is generated from the interaction between the sample light radiation 108 and the tissue sample 190 at all the depths the sample light radiation 108 interacts with the tissue sample 190 along an axial line (A-line) defined between the surface and the bulk of the tissue sample 190. The reflected and/or backscattered light radiation 109 is directed or guided by the same focusing optics of L1 122 and L2 124 and the beam scanner(s) (SC) 126 of the sample arm (S) 120 towards the beam splitter 106, in a direction opposite to the propagating direction of the sample light radiation 108.

The reference light radiation 110 is directed or guided to a reference mirror (RM) 160 through focusing optics, e.g. a pair of lens 152, 154, and a reflected light radiation 111 is generated, as a result of reflection from the reference mirror (RM) 160, and directed or guided towards the beam splitter 106. The back reflected light radiations 111 from the reference arm (R) 150 and the back reflected and/or back scattered light radiation 109 from the sample arm (S) 120 are recombined through the beam splitter 106 to form a spectral interference signal 112 and guided to a spectrometer 170. The spectrometer 170 includes a grating 172, a lens 174 and a detecting element (e.g. a camera) 176. The spectral interference signal 112 is recorded by the spectrometer 170 and processed by a computer (not shown).

The axial line profile (A-line) of the tissue sample 190 can be retrieved by Fourier transform of the spectral interference signal 112. A two-dimensional (2D) cross-sectional image of the tissue sample 190 can be obtained by transversely scanning the sample light radiation 108 using the beam scanner (SC) 126 while continuously acquiring axial line profiles (A-lines). A three-dimensional (3D) image can be obtained by transversely scanning the sample light radiation 108 using 2-axis (X and Y) scanners.

All existing laser scanning OCT systems use spot sources, which are small-sources. Although the existing SD-OCT technology provides a few orders of magnitude higher sensitivity than the TD-OCT technology, thereby enabling higher penetration depth and/or faster imaging speed, the ability of OCT to provide diagnostic information is still limited by its sensitivity, especially when the radiant exposure/irradiance applied to human tissues is restricted to a maximum permissible exposure (MPE) by laser safety regulations such as ANSI (American National Standards Institute) Z136 in the United States and IEC (International Electrotechnical Commission) 60825 internationally.

SUMMARY

According to an embodiment, an optical imaging device is provided. The optical imaging device may include an optics arrangement configured to generate an extended-source illumination pattern including a plurality of separate spectral bands, and to illuminate a respective section of a sample to be imaged with a respective spectral band of the plurality of separate spectral bands, wherein the optics arrangement is further configured to form an interference signal from a sample light comprising respective return lights from respective sections of the sample illuminated by respective spectral bands of the extended-source illumination pattern, and a reference light, and a detector configured to receive the interference signal for generating an image corresponding to the sections of the sample.

According to an embodiment, a method for imaging a sample is provided. The method may include generating an extended-source illumination pattern including a plurality of separate spectral bands, illuminating a respective section of a sample to be imaged with a respective spectral band of the plurality of separate spectral bands, forming an interference signal from a sample light including respective return lights from respective sections of the sample illuminated by respective spectral bands of the extended-source illumination pattern, and a reference light, and generating an image corresponding to the sections of the sample based on the interference signal.

According to an embodiment, a method for generating an image with diffraction limited lateral resolution and coherence length limited axial resolution is provided. The method may be carried out using the optical imaging device as described herein. The method may include scanning an extended-source illumination pattern across an area of a sample such that respective sections of the sample in the area to be imaged are illuminated by an entire spectrum corresponding to the extended-source illumination pattern, and performing a spectral signal remapping algorithm to extract an entire interference spectrum corresponding to a section of the respective sections of the sample for generating an image corresponding to the area of the sample, wherein the interference spectrum is formed from a return light from the section of the sample and a reference light.

BRIEF DESCRIPTION OF THE DRAWINGS

In the drawings, like reference characters generally refer to like parts throughout the different views. The drawings are not necessarily to scale, emphasis instead generally being placed upon illustrating the principles of the invention. In the following description, various embodiments of the invention are described with reference to the following drawings, in which:

FIG. 8A shows a diagram illustrating a spectral remapping method.

FIG. 8B shows a diagram of the DC component of one B-scan frame of a resolution chart while FIG. 8C shows a diagram of the B-scan frame of FIG. 8B after remapping.

DETAILED DESCRIPTION

Figure 1:
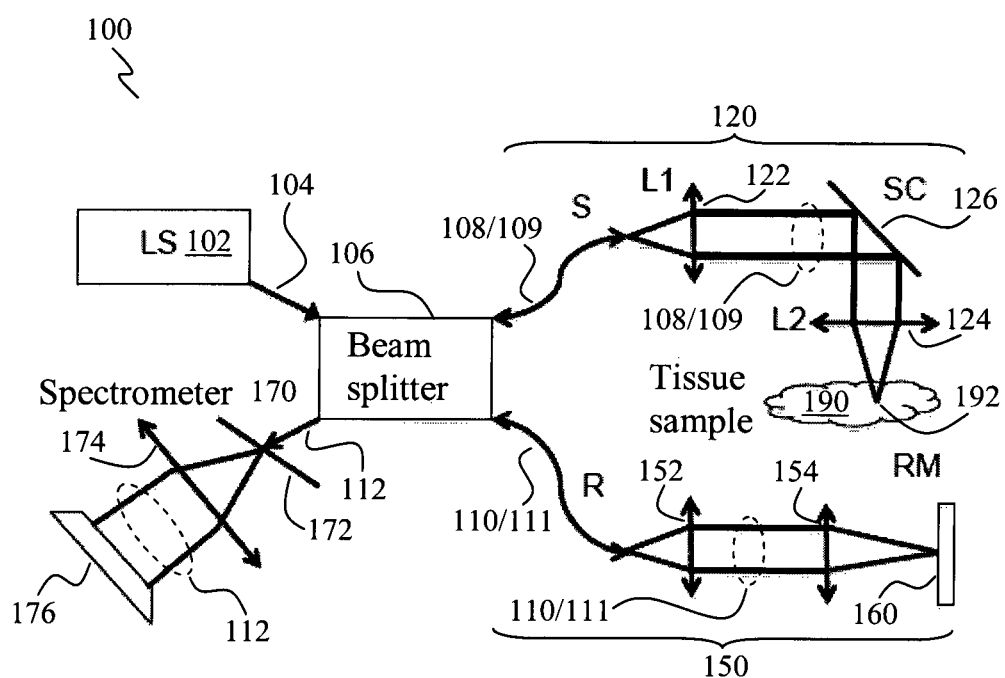
FIG. 1 shows a schematic diagram of a spectral-domain optical coherence tomography (SD-OCT) system of prior art.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

Embodiments described in the context of one of the methods or devices are analogously valid for the other methods or devices. Similarly, embodiments described in the context of a method are analogously valid for a device, and vice versa.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

In the context of various embodiments, the articles "a", "an" and "the" as used with regard to a feature or element include a reference to one or more of the features or elements.

In the context of various embodiments, the phrase "at least substantially" may include "exactly" and a reasonable variance.

In the context of various embodiments, the term "about" or "approximately" as applied to a numeric value encompasses the exact value and a reasonable variance.

As used herein, the term "and/or" includes any and all combinations of one or more of the associated listed items.

As used herein, the phrase of the form of "at least one of A or B" may include A or B or both A and B. Correspondingly, the phrase of the form of "at least one of A or B or C", or including further listed items, may include any and all combinations of one or more of the associated listed items.

Various embodiments may relate to optical coherence tomography (OCT), for example spectral-domain OCT (SD-OCT) or Fourier-domain OCT. As a further example, various embodiments may relate to extended-source SD-OCT and may provide a device or system employing extended-source SD-OCT technology.

Various embodiments may provide an extended-source SD-OCT technology. In various embodiments, an extended-source SD-OCT device or system may be realized by modifying a small-source SD-OCT system. For the extended source SD-OCT system, various embodiments may provide a sample light radiation focusing scheme, a sample light radiation scanning method, and a signal mapping method, as will be described later.

Various embodiments may provide that a sample light radiation produced by the device or system of various embodiments to be safer for biological tissues or samples than an equal-power sample light radiation produced by existing technologies so that the maximum permissible exposure (MPE) for various embodiments may be higher than for existing technologies.

Compared to the existing methods or technologies, various embodiments may enable one or more of the following: (1) a higher maximum permissible exposure (MPE); (2) a higher penetration depth that may be achieved safely without compromising the image acquisition rate; or (3) a higher image acquisition rate that may be achieved safely with a sensitivity at least equal to that of the existing methods.

Conventional SD-OCT devices use a small-source. A "small-source" is a source with an angular subtense, $\alpha$, less than, or equal to, the minimum angular subtense, $\alpha_{min}$, where $\alpha_{min}=1.5$ mrad, as provided in the laser safety regulations IEC 60825. A small-source includes all spot sources or spot illumination patterns, as a spot source or a point source has a typical angular subtense, $\alpha$, much smaller than 1.5 mrad. Generally, a spot illumination has an angular subtense, $\alpha$, of no more than 0.15 mrad, which is ten times smaller than the value for defining a small source.

In contrast, various embodiments provide an extended-source SD-OCT. An "extended source" is a source with an angular subtense, $\alpha$, more than the minimum angular subtense, $\alpha_{min}$. An extended source may include, for example, a line illumination pattern, a square illumination pattern, and a rectangular illumination pattern.

Angular subtense is defined as the visual angle subtended by a source at an eye of an observer, in which the source is located at a distance greater than 100 mm from the pupil of the eye. Angular subtense, $\alpha$, may be defined as (diameter of source/100 mm).

Figure 2A:
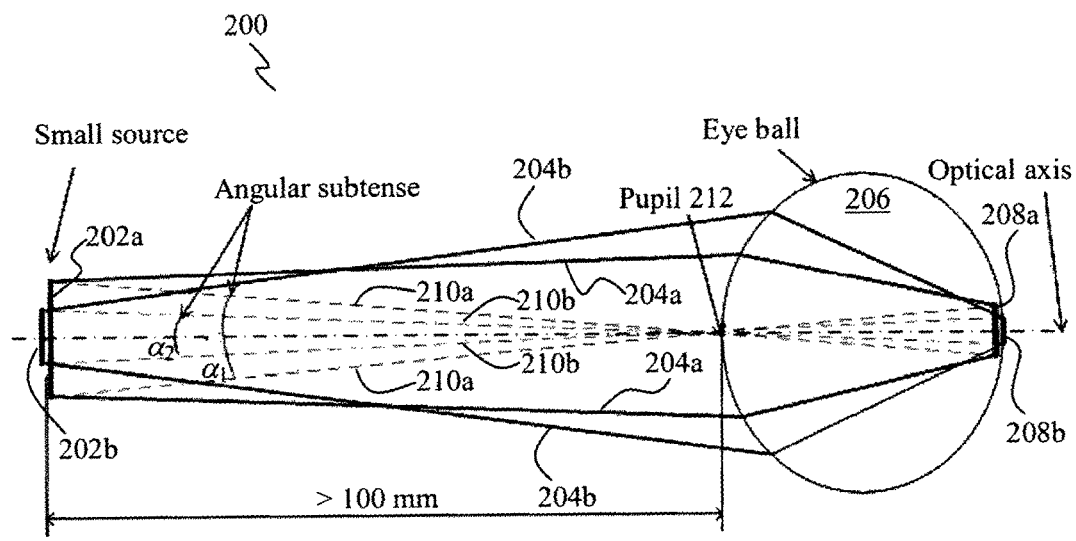
FIG. 2A shows a schematic diagram illustrating small-source viewing.

FIG. 2A shows a schematic diagram 200 illustrating small-source viewing. For a small-source 202a using a low numeral aperture (NA) lens, as viewed by an observer's eye, light (represented by solid line 204a) may be traced from the small-source 202a towards the eye ball 206 of the observer's eye to form an image 208a. Light (represented by dashed lines 210a) may be traced from the image 208a through the pupil 212. The angle subtended by the dashed lines 210a is the angular subtense, $\alpha_1$, of the small-source 202a.

For a small-source 202b using a high numeral aperture (NA) lens, as viewed by an observer's eye, light (represented by solid line 204b) may be traced from the small-source 202b towards the eye ball 206 of the observer's eye to form an image 208b. Light (represented by dashed lines 210b) may be traced from the image 208b through the pupil 212. The angle subtended by the dashed lines 210b is the angular subtense, $\alpha_2$, of the small-source 202b. By the use of a high NA lens, the diverging angle is larger but if it is a laser source, the diameter or size of the source becomes smaller. Therefore, the corresponding angular subtense actually becomes smaller as the definition of angular subtense is (diameter of source/100 mm). Therefore, $\alpha_2$ is less than $\alpha_1$, where both $\alpha_2$ and $\alpha_1$ are less than $\alpha_{min}$.

Figure 2B:
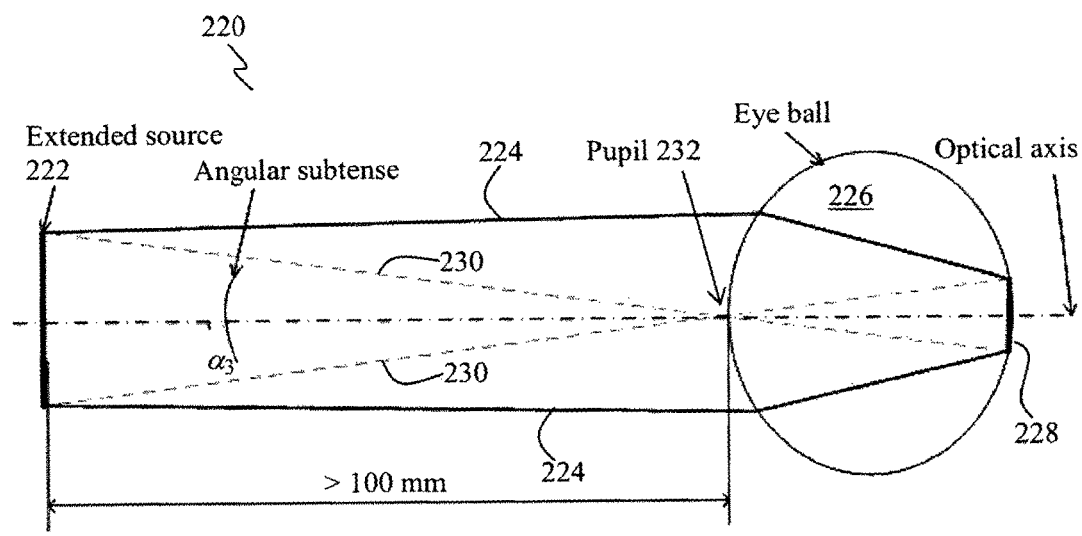
FIG. 2B shows a schematic diagram illustrating extended-source viewing.

FIG. 2B shows a schematic diagram 220 illustrating extended-source viewing. For an extended-source 222, as viewed by an observer's eye, light (represented by solid line 224) may be traced from the extended-source 222 towards the eye ball 226 of the observer's eye to form an image 228. Light (represented by dashed lines 230) may be traced from the image 228 through the pupil 232. The angle subtended by the dashed lines 230 is the angular subtense, $\alpha_3$, of the extended-source 222. $\alpha_3$ is more than each of $\alpha_1$ and $\alpha_2$, and $\alpha_3$ is also more than $\alpha_{min}$. In the case of an extended source, the size of the extended-source is larger than that of a small-source, and so the corresponding angular subtense is larger.

Sensitivity of an SD-OCT system may be defined as the signal-to-noise ratio (SNR) for a perfect sample reflector. The SD-OCT image quality may be directly related to the system sensitivity, for example for Doppler SD-OCT and polarization-sensitive SD-OCT. Sensitivity of a SD-OCT system may also determine its penetration depth. As the signal power may decay exponentially as a function of tissue or sample depth due to light scattering and absorption of the signal by the tissue, at a certain tissue or sample depth, the signal power may drop below the noise power such that it may become challenging for tissue information to be retrieved or possibly the tissue information cannot be retrieved. This tissue depth, beyond which the noise power may dominate compared to the signal power provided by the power source of the SD-OCT system, is the penetration depth of the SD-OCT system.

Deep tissue structures such as the optic nerve head (ONH), the lamina cribrosa (LC) and the posterior sclera (PS) are thought to be important biomechanical players in ocular disorders such as glaucoma, myopia, and papilledema. The sensitivity of current SD-OCT technology is just sufficient to visualize the upper portion of these deep tissue structures, and the image quality of the detectable portion is still inferior to that of histology. This limitation in sensitivity not only precludes the possibility of detecting early sign(s) of these diseases and clinical hypothesis testing using SD-OCT, but also may result in clinical misinterpretation and morphometric (parameterization) errors.

Generally, there are two practical ways to enhance the SD-OCT sensitivity based on the current commercially available devices: increasing the sample light radiation applied on the tissue and increasing the exposure time of the sample light radiation. However, the radiant exposure/irradiance applied to human tissues (for example eye and skin) is restricted to a maximum permissible exposure (MPE) by laser safety regulations such as ANSI Z136 in the United States and IEC 60825-1 internationally. Additionally, increasing the exposure time reduces the image acquisition rate, thereby increasing motion artifacts in the image, especially for three-dimensional imaging.

According to IEC 60825-1, the maximum permissible exposure (MPE) at the cornea for direct exposure to laser radiation within a wavelength or spectral range of 700 nm-1400 nm, for a time duration, $t<T_2$, may be determined as $$\text{MPE}=18t^{0.75} C_4 C_6 J \cdot m^{-2} \quad \text{(Equation 1)},$$

where t is the exposure time, $C_4$ is the correcting factor for different wavelengths, and $C_6$ is the correcting factor for extended sources.

$T_2$ may be defined as:

$$T_2=10\times 10^{[(\alpha-\alpha min)/98.5]} s \quad \text{(Equation 2)},$$

where $\alpha$ is the angular subtense and $\alpha_{min}$ is the minimum angular subtense, where $\alpha_{min}=1.5$ mrad. $\alpha_{min}$ refers to the value of angular subtense of the apparent source above which a source is considered an extended source. For $\alpha<1.5$ mrad, $T_2=10$ s, and for $\alpha>100$ mrad, $T_2=100$ s.

$C_4$ may be defined, for a spectral range of 700 nm-1050 nm, as:

$$C_4 = 10^{0.0020(\lambda - 700)} \quad \text{(Equation 3)},$$

where $\lambda$ is the wavelength. For a spectral range of 1050 nm-1400 nm, $C_4 = 5$.

For an extended-source, such as an extended-source laser radiation (for example, diffuse reflection viewing) at wavelengths, $\lambda$, from about 400 nm to about 1 400 nm, the thermal ocular hazard MPEs may be increased by the factor $C_6$ provided that the angular subtense, $\alpha$, of the source (measured at the viewer's eye) is greater than $\alpha_{min}$, where $\alpha_{min}$ is equal to 1.5 mrad. The correction factor $C_6$ is given as:

$C_6 = 1$ for $\alpha < \alpha_{min}$ $C_6 = \alpha/\alpha_{min}$ for $\alpha_{min} < \alpha < \alpha_{max}$ $C_6 = \alpha_{max}/\alpha_{min} (\approx 66.7)$ for $\alpha > \alpha_{max}$ \quad (Equation 4), where $\alpha_{max} = 100$ mrad. $\alpha_{max}$ refers to a maximum angular subtense which is the value of angular subtense of the apparent source above which the MPEs are independent of the source size.

Figure 3A:
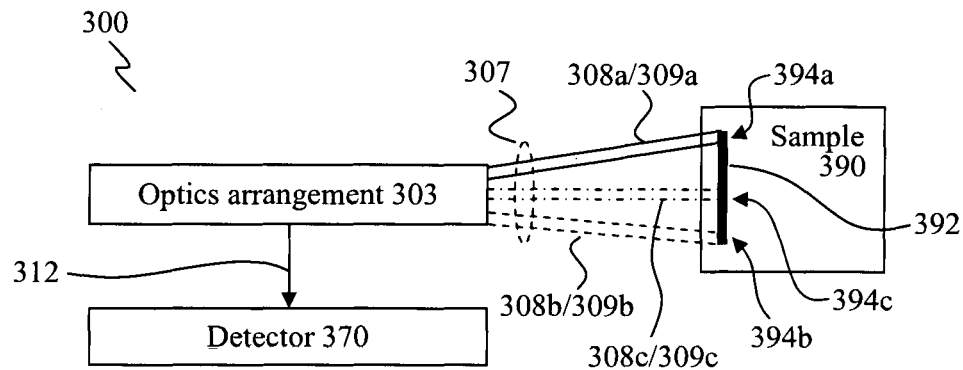
FIG. 3A shows a schematic cross-sectional view of an optical imaging device, according to various embodiments.

FIG. 3A shows a schematic cross-sectional view of an optical imaging device 300, according to various embodiments. The optical imaging device 300 includes an optics arrangement 303 configured to generate an extended-source illumination pattern 307 including a plurality of separate spectral bands 308a, 308b, 308c, and to illuminate a respective section 394a, 394b, 394c of a sample 390 to be imaged with a respective spectral band 308a, 308b, 308c of the plurality of separate spectral bands 308a, 308b, 308c, wherein the optics arrangement 303 is further configured to form an interference signal 312 from a sample light comprising respective return lights 309a; 309b, 309c from respective sections 394a, 394b, 394c of the sample 390 illuminated by respective spectral bands 308a, 308b, 308c of the extended-source illumination pattern 307, and a reference light, and a detector 370 configured to receive the interference signal 312 for generating an image corresponding to the sections 394a, 394b, 394c of the sample 390.

In other words, an optical imaging device 300 may be provided. The optical imaging device 300 may include an optics arrangement 303, which for example may have an assembly of optical elements. The optics arrangement 303 may be configured to generate an extended-source illumination pattern (e.g. a sample light radiation) 307 for illuminating a sample 390 that is to be imaged.

The extended-source illumination pattern 307 may include individual spectral bands 308a, 308b, 308c separate from each other. By "separate", it is meant that the plurality of spectral bands 308a, 308b, 308c may be distinct from each other and respective spectral bands 308a, 308b, 308c may propagate through different optical paths. Further, this means that respective portions of the extended-source illumination pattern 307 may be defined by respective spectral bands 308a, 308b, 308c. There may be spatial overlapping among spectral bands 308a, 308b, 308c. Further, by "separate", it does not necessarily mean that the plurality of spectral bands 308a, 308b, 308c may be discontinuous spectrally or spatially.

In various embodiments, the entire extended-source illumination pattern 370 generated may illuminate the sample 390 at any one time. This may mean that the plurality of separate spectral bands 308a, 308b, 308c may simultaneously illuminate the sample 390 such that the respective sections 394a, 394b, 394c of the sample 390 may be illuminated by the respective spectral bands 394a, 394b, 394c at least substantially similar time or simultaneously.

The optics arrangement 303 may be further configured to illuminate a respective section 394a, 394b, 394c of the sample 390 to be imaged with a respective spectral band 308a, 308b, 308c of the plurality of separate spectral bands 308a, 308b, 308c. For example, as shown in FIG. 3A, the spectral band 308a may illuminate section 394a of the sample 390, the spectral band 308b may illuminate section 394b, while the spectral band 308c may illuminate section 394c. As a non-limiting example, the extended-source illumination pattern 307 may illuminate the sample in the form of a line illumination pattern 392. A return light 309a, 30b, 309c may be induced or generated from each section 394a, 394b, 394c of the sample 390 resulting from interaction between the respective spectral bands 308a, 308b, 308c of the extended-source illumination pattern 307 and the respective sample sections 394a, 394b, 394c. For example, a return light 309a may originate from the sample section 394a. Each return light 309a, 30b, 309c may include information associated with the respective sample sections 394a, 394b, 394c illuminated by the respective spectral bands 308a, 308b, 308c. It should be appreciated that the term "section" in relation to a sample may include a point on the sample.

The optics arrangement 303 may be further configured to form an interference signal (or a spectral interference signal) 312 from a sample light including respective return lights 309a, 309b, 309c from respective sections 394a, 394b, 394c of the sample 390 illuminated by respective spectral bands 308a, 308b, 308c of the extended-source illumination pattern 307, and a reference light. For example, a light (e.g. a reference light radiation) may be reflected from a reference point or plane (e.g. by means of a reflector or a mirror) to form a reference light. In various embodiments, the sample light may originate from a sample arm (S) or a sample optical path while the reference light may originate from a reference arm (R) or a reference optical path, where the sample arm (S) and the reference arm (R) may define an interferometer or an interferometric arrangement. In various embodiments, the reference light may interfere with the sample light by means of the interferometric arrangement to form the interference signal 312. The interference signal 312 therefore may be an interferometric signal.

The interference signal 312 may include a signal resulting from interference between the sample light and the reference light, which may be used for generating an image of the sample 390. It should be appreciated that constructive interference and/or destructive interference between the sample light and the reference light may carry information which may be used for generating the image. Further, it should be appreciated that for a spectral interference or spectral domain OCT (SD-OCT) device, the path length difference between the sample light and the reference light may be large.

The optical imaging device 300 may further include a detector 370 configured to receive the interference signal 312 so as to form an image of the sections 394a, 394b, 394c of the sample 390. The detector 370 may obtain from the interference signal 312 spectral information associated with respective sample sections 394a, 394b, 394c illuminated by respective spectral bands 308a, 308b, 308c.

In the context of various embodiments, the term "extended-source" may mean a source with an angular subtense, $\alpha$, more than the minimum angular subtense, $\alpha_{min}$, where $\alpha_{min} = 1.5$ mrad. Accordingly, an extended-source illumination pattern may mean an illumination pattern that may subtend an angle at a sample (e.g. eye) greater than the minimum angular subtense, $\alpha_{min}$, of 1.5 mrad. In other words, an extended-source illumination pattern, with respect to a sample, may provide an angular subtense, $\alpha$, of more than 1.5 mrad (i.e. $\alpha$>1.5 mrad). In various embodiments, angular subtense may be defined as (diameter of source/100 mm).

In the context of various embodiments, the extended-source illumination pattern 307 may provide an illumination pattern other than a spot illumination, which is a small-source as a-spot source or a point source has a typical angular subtense much smaller than 1.5 mrad ($\alpha_{min}$).

In the context of various embodiments, the extended-source illumination pattern 307 may include but not limited to a line illumination pattern, a square illumination pattern, or a rectangular illumination pattern.

In the context of various embodiments, the extended-source illumination pattern 307 may penetrate into the bulk or depth of the sample 390, meaning that the extended-source illumination pattern 307 may provide sub-surface illumination.

In various embodiments, the optics arrangement, 303 may include an optical element (D) configured to generate the extended-source illumination pattern 307. The optical element may be arranged to receive a light and to generate the extended-source illumination pattern 307 from the light received. For example, the light may be a small source (e.g. a spot source), which may be shaped by the optical element to generate the extended-source illumination pattern 307. In this way, the radiation spectrum of the small source may be spread by the optical element to generate the extended-source illumination pattern 307, for example in the form of a line. As a non-limiting example, the optical element may be a diffraction grating.

In various embodiments, the optical element may include a dispersive element. The dispersive element may include at least one of a refractive element (e.g. a prism) or a diffractive element (e.g. a grating).

In various embodiments, the optics arrangement 303 may be further configured to scan the extended-source illumination pattern 307 across at least a portion of the sample 390. The optics arrangement 303 may include a scanning device (SC) that may be movable to scan the extended-source illumination pattern 307 across at least a portion of the sample 390. The scanning device may act as a light director, and may be arranged to re-direct the extended-source illumination pattern 307 towards the sample 390, for example by way of reflection. The scanning device may include a mirror or a reflector to reflect light.

For example, by scanning the extended-source illumination pattern 307 across at least a portion of the sample 390, a first group of sections of the sample 390 may be illuminated and then scanning of the extended-source illumination pattern 307 may be carried out to illuminate a second group of sections of the sample 390. It should be appreciated that some sections of the first group of sections may overlap with some sections of the second group of sections. This may mean that some sections 394a, 394b, 394c may be illuminated during the scanning process, possibly with a different spectral band 308a, 308b, 308c during each scan or illumination of the same section at different scanning times.

In various embodiments, the optics arrangement 303 may include a collimation lens configured to produce a collimated light from which the extended-source illumination pattern 307 may be generated.

In various embodiments, the optics arrangement 303 may include a beam splitter arranged to receive and split a light into a first light from which the extended-source illumination pattern 307 may be generated, and a second light from which the reference light may be derived. This may mean that the sample light may be derived from the first light produced by the beam splitter. In various embodiments, the collimation lens may be arranged to receive the first light from the beam splitter and to produce the collimated light from which the extended-source illumination pattern 307 may be generated. In the context of various embodiments, the sample light and the reference light may interfere at the beam splitter to form the interference signal 312.

In the context of various embodiments, the optics arrangement 303 may include a relay optics assembly optically coupled to the extended-source illumination pattern 307. The extended-source illumination pattern 307 may propagate through the relay optics assembly. The relay optics assembly may interact with the extended-source illumination pattern 307, for example the relay optics assembly may manipulate or act on the extended-source illumination pattern 307. For example, the relay optics assembly may focus and collimate the plurality of separate spectral bands 308a, 308b, 308c of the extended-source illumination pattern 307. In this way, an intermediate or apparent source source may be generated.

In various embodiments, the optics arrangement 303 may include a-beam splitter arranged to receive and split light corresponding to the extended-source illumination pattern 307 into a first portion for illuminating the respective sections 394a, 394b, 394c of the sample 390, and a second portion from which the reference light may be derived. In the context of various embodiments, the sample light and the reference light may interfere at the beam splitter to form the interference signal 312.

In various embodiments, the optics arrangement 303 may include focusing optics (e.g. having at least an objective lens) for focusing the extended-source illumination pattern 307 onto a focal plane on the sample 390 corresponding to the sections 394a, 394b, 394c of the sample 390.

In various embodiments, the detector 370 may include a grating arranged to spectrally disperse the interference signal 312.

In the context of various embodiments, the detector 370 may be a spectrometer.

In the context of various embodiments, the detector 370 may include a detecting element such as a camera (e.g. a line camera).

In various embodiments, the optical imaging device 300 may further include a processor configured to obtain information (e.g. spectral information) corresponding to the sections 394a, 394b, 394c of the sample 390 from the interference signal 312 for generating the image corresponding to the sections 394a, 394b, 394c of the sample 390. The processor may be configured to obtain, from the interference signal 312, information corresponding to the respective section 394a, 394b, 394c of the sample 390 imaged with the respective spectral band 308a, 308b, 308c, and to interpolate the obtained information in time domain to obtain information corresponding to the respective section 394a, 394b, 394c for a subsequent spectral band adjacent (e.g. immediately adjacent) to the respective spectral band 308a, 308b, 308c. In the context of various embodiments, the processor may be configured to perform Fourier transform on the interference signal 312.

In various embodiments, the optical imaging device 300 may further include a light source (LS), wherein the optics arrangement 303 may be configured to generate the extended-source illumination pattern 307 based on a light produced by the light source. As a non-limiting example, the light source may be a diode laser source.

In the context of various embodiments, the extended-source illumination pattern 307 may be an oblong illumination pattern. This may mean that the extended-source illumination pattern 307 may have a shape or form elongated in one direction, e.g. a rectangular illumination pattern. In various embodiments, the extended-source illumination pattern 307 may be a line (linear) illumination pattern.

In the context of various embodiments, the extended-source illumination pattern 307 may have a length with a corresponding angular dimension that is more than 1.5 mrad (i.e. >1.5 mrad). For example, the extended-source illumination pattern 307 may have a length with a corresponding angular dimension >1.5 mrad, and a width with a corresponding, angular dimension <1.5 mrad.

In the context of various embodiments, the optical imaging device 300 may be an optical coherence tomography (OCT) device. As an extended-source illumination pattern 307 is provided onto a sample 390, the OCT device may be an extended-source OCT. Further, as information associated with respective sample sections 394a, 394b, 394c may be encoded in terms of wavelengths (spectral), accordingly, the optical imaging device 300 may be an extended-source spectral domain OCT device.

Figure 3B:
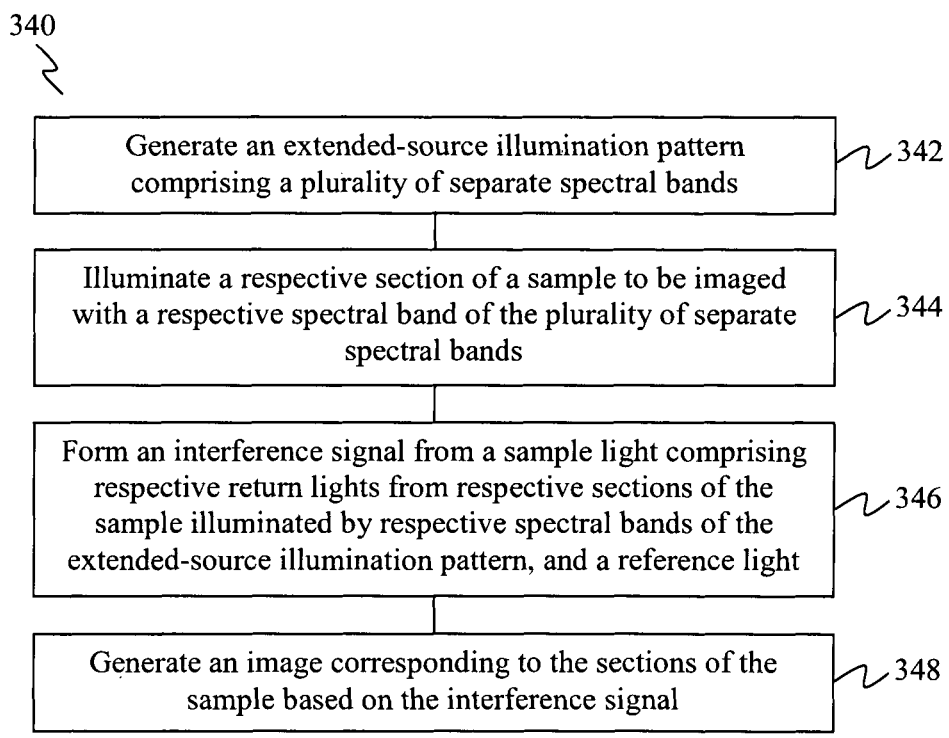
FIG. 3B shows a flow chart illustrating a method for imaging a sample, according to various embodiments.

FIG. 3B shows a flow chart 340 illustrating a method for imaging a sample, according to various embodiments.

At 342, an extended-source illumination pattern is generated, where the extended-source illumination pattern includes a plurality of separate spectral bands.

At 344, a respective section of a sample to be imaged is illuminated with a respective spectral band of the plurality of separate spectral bands.

At 346, an interference signal is formed from a sample light including respective return lights from respective sections of the sample illuminated by respective spectral bands of the extended-source illumination pattern, and a reference light.

At 348, an image corresponding to the sections of the sample is generated based on the interference signal.

The method may further include scanning the extended-source illumination pattern across at least a portion of the sample.

In various embodiments, a collimated light may be provided or generated, and the extended-source illumination pattern may be generated from the collimated light. In other words, a collimated light may be employed to generate the extended-source illumination pattern.

In various embodiments, a light may be received, for example from a light source, and the light may be split into a first light from which the extended-source illumination pattern may be generated, and a second light from which the reference light may be derived.

In various embodiments, the plurality of separate spectral bands of the extended-source illumination pattern may be focused and collimated. This may generate an apparent or intermediate light source for illuminating the sample.

In various embodiments, light corresponding to the extended-source illumination pattern may be split into a first portion for illuminating the respective sections of the sample, and a second portion from which the reference light may be derived.

In various embodiments, the method may further include focusing the extended-source illumination pattern onto a focal plane on the sample corresponding to the sections of the sample.

In various embodiments, the interference signal may be spectrally dispersed. This may be carried out prior to generating the image corresponding to, the sections of the sample.

In, various embodiments, at 348, for generating the image, information corresponding to the sections of the sample may be obtained from the interference signal. This may include obtaining, from the interference signal, information corresponding to the respective section of the sample imaged with the respective spectral band, and interpolating the obtained information in time domain to obtain information corresponding to the respective section for a subsequent spectral band adjacent to the respective spectral band. In various embodiments, a Fourier transform may be performed on the interference signal to obtain the information.

In various embodiments, the extended-source illumination pattern may be an oblong illumination pattern, e.g. a line illumination pattern. The extended-source illumination pattern may have a length with a corresponding angular dimension that is more than 1.5 mrad (i.e. >1.5 mrad).

While the method described above is illustrated and described as a series of steps or events, it will be appreciated that any ordering of such steps or events are not to be interpreted in a limiting sense. For example, some steps may occur in different orders and/or concurrently with other steps or events apart from those illustrated and/or described herein. In addition, not all illustrated steps may be required to implement one or more aspects or embodiments described herein. Also, one or more of the steps depicted herein may be carried out in one or more separate acts and/or phases.

Various embodiments may also provide a method for generating an image with diffraction limited lateral resolution and coherence length limited axial resolution using the optical imaging device described herein. The method may include scanning an extended-source illumination pattern across an area of a sample such that respective sections (or points) of the sample in the area to be imaged are illuminated by an entire spectrum corresponding to the extended-source illumination pattern, and performing a spectral signal remapping algorithm to extract an entire interference spectrum corresponding to a section of the respective sections of the sample for generating an image corresponding to the area of the sample, wherein the interference spectrum is formed from a return light from the section of the sample and a reference light. It should be appreciated that the spectral signal remapping algorithm may be carried out to extract the entire interference spectrum corresponding to any section of the sample in the area to be imaged.

Various embodiments may also provide a method for generating images with diffraction limited lateral resolution and coherence length limited axial resolution based on the optical imaging device described herein. The method may include a mechanism that may scan the extended-source (or an extended-source illumination pattern) so that all the points (or sections) of a sample (e.g. a tissue sample) in the imaged area may be illuminated by entire spectrum of the light source, and a spectral signal remapping algorithm to extract the entire interference spectrum corresponding to any point of the sample in the imaged area.

A sample light radiation focusing scheme, a sample light radiation scanning method, and a signal mapping method may be provided for the device or system of various embodiments.

In the existing SD-OCT technology, a small source (angular subtense $\alpha<1.5$ mrad) is used as the sample light radiation field. Normally, it is a point source of a laser diode or a single mode fiber pinhole. However, for various embodiments, the sample light radiation field (apparent source as defined in IEC 60825) is modified to a linear source (angular subtense $\alpha$>1.5 mrad), so that the apparent source for the SD-OCT device of various embodiments qualifies as an extended source according to the safety regulations such as IEC 60825-1. In other words, an extended source is employed for the device of various embodiments.

The sample light radiation focusing scheme of various embodiments will now be described by way of the following non-limiting examples.

Figure 4A:
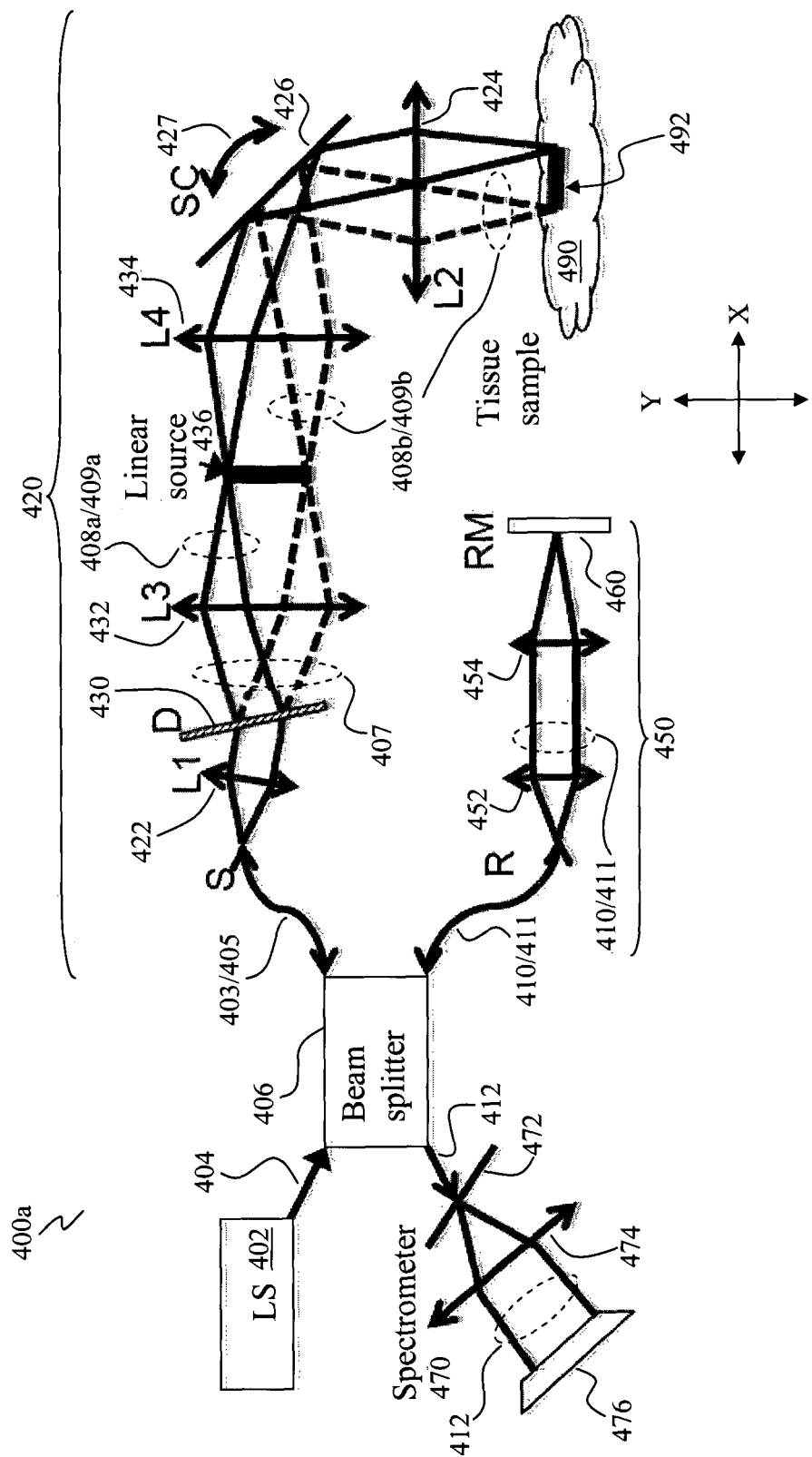
FIG. 4A shows a schematic view of an optical imaging device, according to various embodiments.

FIG. 4A shows a schematic view of an optical imaging device 400a, according to various embodiments. The optical imaging device 400a may be an extended-source SD-OCT device. The optical imaging device 400a includes a light source (LS) 402 which may provide a light 404, for example in the form of a small-source, to a beam splitter 406. The beam splitter 406 may split the light 404 into two 403, 410, which are respectively provided to a sample arm (S) 420 and a reference arm (R) 450 of the optical imaging device 400a. Light 403 may be collimated by a collimation lens (L1) 422, which then passes through a dispersive element (D) 430. The dispersive element (D) 430 may include prism(s), grating(s) or other dispersive component(s). The dispersive element (D) 430 may spread the radiation or light spectrum of the small source (light 403) to an extended-source, e.g. a line or linear source 436. In details, the dispersive element (D) 430 may generate an extended-source illumination pattern 407 from the light 403. As a result of passing through the dispersive element (D) 430, spectral bands making up the extended-source illumination pattern 407 may become separate from each other. As shown in FIG. 4A, the illustrated extreme spectral bands 408a, 408b are separate from each other. A relay optics assembly having relay optics lens (L3 and L4) may be provided such that the lens L3 432 may focus the plurality of spectral bands, including spectral bands 408a, 408, to form an intermediate or apparent linear source 436, which is then collimated by the lens L4 434. The spectral bands, including bands 408a, 408b, may then be directed by a beam scanner or a scanning device (SC) 426 towards a sample (e.g. a tissue sample) 490 to be imaged, forming a line illumination 492 at the sample 490. Light radiation at a given point within the line 436 may have a narrow spectral line width. The center wavelength and the line width at a given point in the linear source 436 may be determined by the dispersive property of the dispersive element (D) 430 and the focusing power of the relay lens L3 432. The linear source 436 may be located at a plane conjugated with the sample 490, so that on the sample 490, the illumination light radiation field may also be a line.

An objective lens (L2) 424 may be arranged to focus the extended-source illumination pattern 407 including the spectral bands towards a focal plane on the sample 490. Respective spectral bands of the extended-source illumination pattern 407 may illuminate respective sections of the sample along the line illumination 492. The scanning device (SC) 426 may be moved, for example in directions represented by the arrow 427, during the scanning process so as to scan different parts of the sample 490 so that a two or three-dimensional image of the sample 490 may be formed.

Interaction between respective spectral bands and the respective sample sections result in respective return lights being generated. Each return light may include light reflected and/or light scattered from the sample section. Respective return lights, for example 409a, 409b, may propagate through at least substantially similar optical paths as for the respective spectral bands, but in an opposite direction, through the objective lens (L2) 424, the scanning device (SC) 426, the relay optics lens L4 434 and L3 432, the dispersive element (D) 430 and the lens L1 422 towards the beam splitter 406 to define a sample light 405.

In the reference arm (R) 450, light 410 may propagate through a pair of lens, for example a collimation lens 452 which may collimate the light 410, and a focusing lens 454 which may then focus the collimated light onto a reference mirror (RM) 460. Light 410 incident on the reference mirror 460 is reflected by the reference mirror 460, which then propagates through the collimation lens 452 and the focusing lens 454 towards the beam splitter 406 to define a reference light 411.

At the beam splitter 406, the sample light 405 and the reference light 411 may interfere with each other or may be combined to form an interference signal 412 to be received by a spectrometer 470 acting as a detector. The spectrometer 470 may include a grating 472 to spectrally disperse the interference signal 412, which is then collimated by a collimation lens 474 prior to being detected or captured by a detecting element 476, e.g. a camera.

Processing may be carried out to obtain spectral information corresponding to the sample 490 illuminated by the extended-source illumination pattern 407 from the interference signal 412.

According to the safety regulations defined in IEC 60825, for the determination of MPE for non-circular sources, the value of the angular subtense, $\alpha$, of a linear source may be determined by an arithmetic mean of the two angular dimensions (e.g. height and width) of the source. Any angular dimension that is greater than $\alpha_{max}$ or less than $\alpha_{min}$ shall be limited to $\alpha_{max}$ or $\alpha_{min}$ respectively, prior to calculating the arithmetic mean. For extended-source SD-OCT, the angular subtense of the linear source 436 along the X dimension (horizontal direction as indicated in FIG. 4A), $\alpha_X$, is less than a (i.e. $\alpha_X<\alpha_{min}$), such that $\alpha_X=\alpha_{min}$, while the angular subtense of the linear source 436 along the Y dimension (vertical direction indicated in FIG. 4A), $\alpha_Y$, is more than $\alpha_{min}$ (i.e. $\alpha_Y>\alpha_{min}$), such that the angular subtense, $\alpha$, of the linear source 436 may be as defined below:

$$\alpha = 1/2(\alpha_X + \alpha_Y) \quad \text{(Equation 5)}$$
$$= 1/2(\alpha_{min} + \alpha_Y) > \alpha_{min}.$$

Based on Equation 4, the correction factor $C_6$ for the linear source is $C_6>1$, while for a small source, $C_6=1$. Therefore, the correction factor $C_6$ for extended-source SD-OCT of various embodiments may be larger than that of small-source SD-OCT.

As a non-limiting example, if the Y dimension of the linear source 436 is about 0.5 mm, the angular subtense, $\alpha_Y$, along the Y direction is (0.5 mm/100 mm)=50 mrad, because the angular subtense is determined at a point not less than 100 mm from the apparent source (or at the exit window or lens of the product or device if the apparent source is located at a distance greater than 100 mm within the window or lens), as defined in IEC 60825. Based on Equation 5, the angular subtense, $\alpha$, for the linear source is ($\alpha=\frac{1}{2}$ ($\alpha_{min}$+ $\alpha_Y$)=(1.5 mrad+50 mrad)=25.75 mrad). Based on Equation 4, $C_6$ for the linear source 436 may be defined as ($C_6=\alpha/\alpha_{min}$=25.75 mrad/1.5 mrad=17.17) As $C_6$ for small-source SD-OCT is 1, the MPE at the cornea for the extended-source SD-OCT is 17.17 times higher than small-source SD-OCT. Given that a SD-OCT system is shot-noise limited, the maximum sensitivity of an extended-source SD-OCT device or system may be 17.17 times or 12.5 dB higher than that of the small-source SD-OCT system. Examples of simulation results for a small-source source SD-OCT system and an extended-source source SD-OCT system are shown in FIGS. 5A and 5B.

Figure 5A:
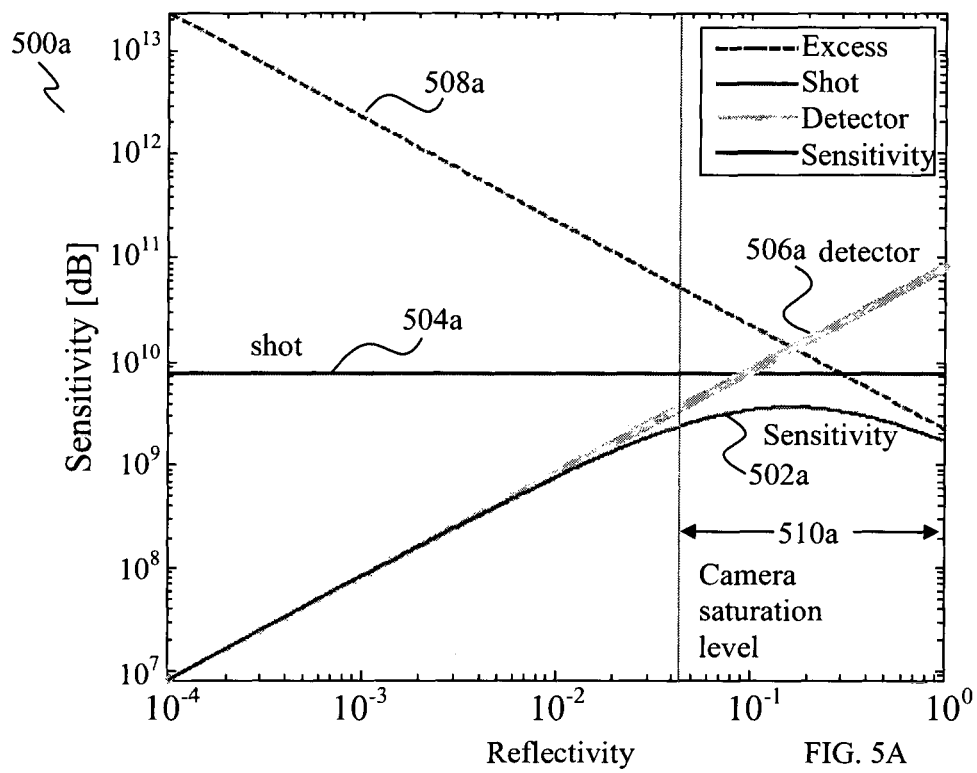
FIG. 5A shows a plot of simulation results for sensitivity as a function of reference reflectivity for a small-source spectral-domain optical coherence tomography (SD-OCT) device.
Figure 5B:
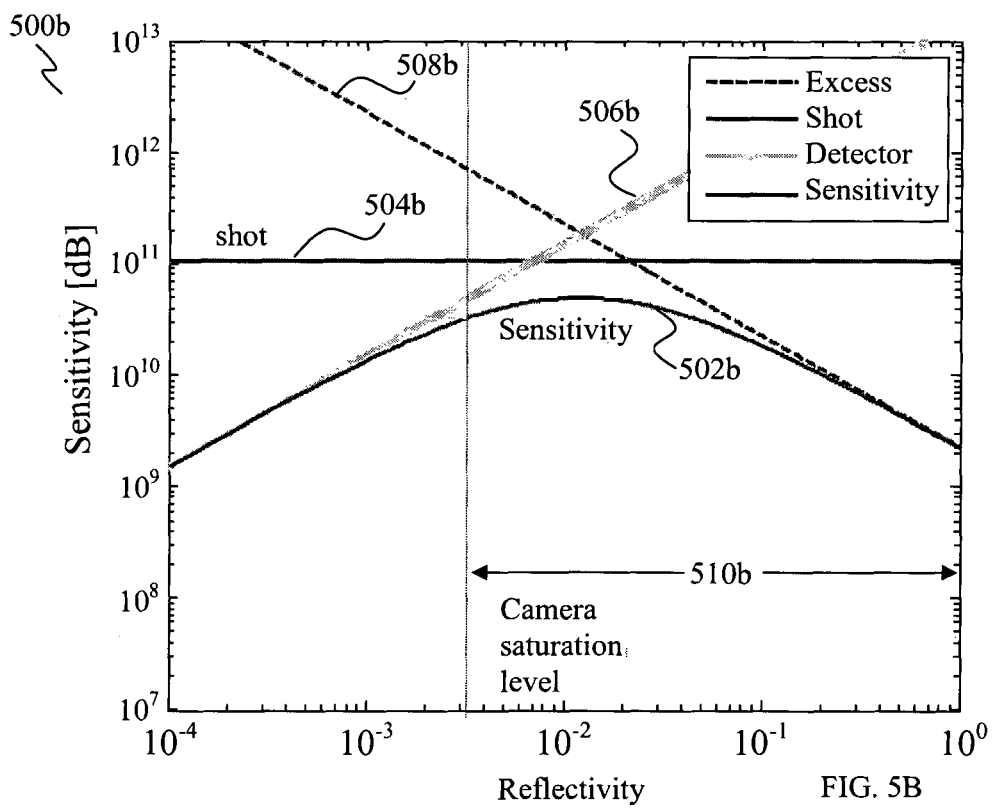
FIG. 5B shows a plot of simulation results for sensitivity as a function of reference reflectivity for an extended-source spectral-domain optical coherence tomography (SD-OCT) device.

FIGS. 5A and 5B show plots 500a, 500b of simulation results for sensitivity (theoretical sensitivity) 502a, 502b as a function of reference reflectivity for a small-source (SD-OCT) device and an extended-source SD-OCT device, respectively. Also shown in FIGS. 5A and 5B are results 504a, 504b for shot noise, results 506a, 506b for detector noise and results 508a, 508b for "excess noise".

For both cases of the small-source (SD-OCT) and extended-source SD-OCT devices, maximum sensitivity may be achieved at the camera saturation level, as represented by 510a, 510b. Camera parameters (e.g. corresponding to the detecting element 476) may be obtained from the specifications of E2V AVIIVA EM4 BA9. The light power on the sample is about 600 µW for small-source SD-OCT and about 10.698 mW for extended source SD-OCT. The exposure time is about 50 µsec. The spectrometer efficiency is about 0.5 and the grating efficiency corresponding to the grating 472 is about 0.7.

Another way to understand the sensitivity advantage of extended-source SD-OCT over small-source SD-OCT is as, described below. Assuming that the total Y-direction scanning range is about 6 mm and 1024 A-lines are acquired per scan, the effective exposure time of extended-source SD-OCT is 6 mm/0.5 mm×1024=83 times larger than that of small-source SD-OCT. According to Equation 1, the MPE for extended-source SD-OCT may be $83^{0.75}$=28 times larger than that of small source SD-OCT, which means an approximately 14.5 dB sensitivity increase.

Figure 4B:
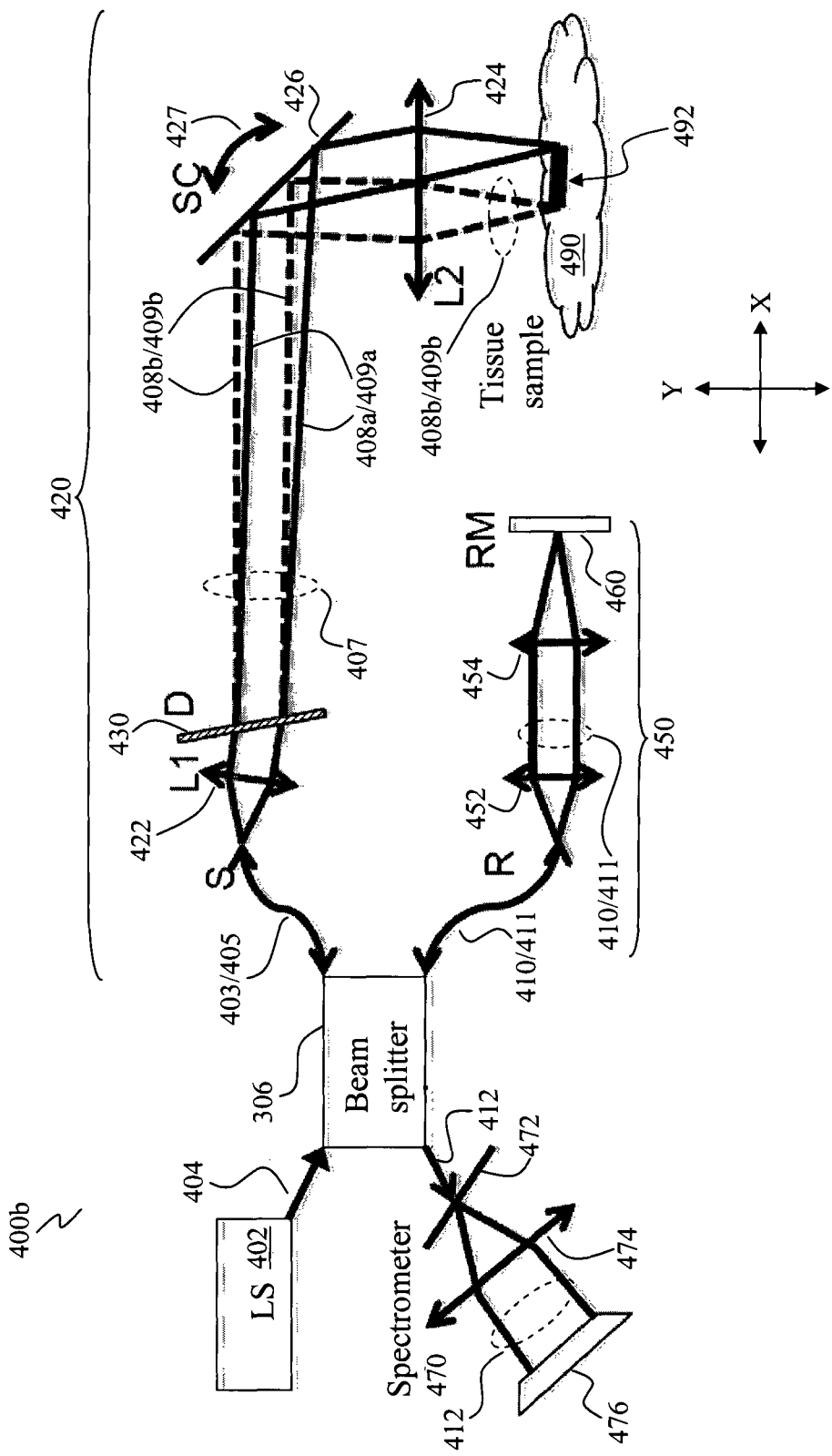
FIG. 4B shows a schematic view of an optical imaging device, according to various embodiments.

FIG. 4B shows a schematic view of an optical imaging device 400b, according to various embodiments. The optical imaging device 400b may be an extended-source SD-OCT device, for example a line-source SD-OCT device. The optical imaging device 400b may be similar to the optical imaging device 400a, for example in terms of optical elements, optical arrangement and operation, except that the relay optics assembly having lens L3 and L4, as incorporated in the optical imaging device 400a, is not provided in the optical imaging device 400b.

Figure 4C:
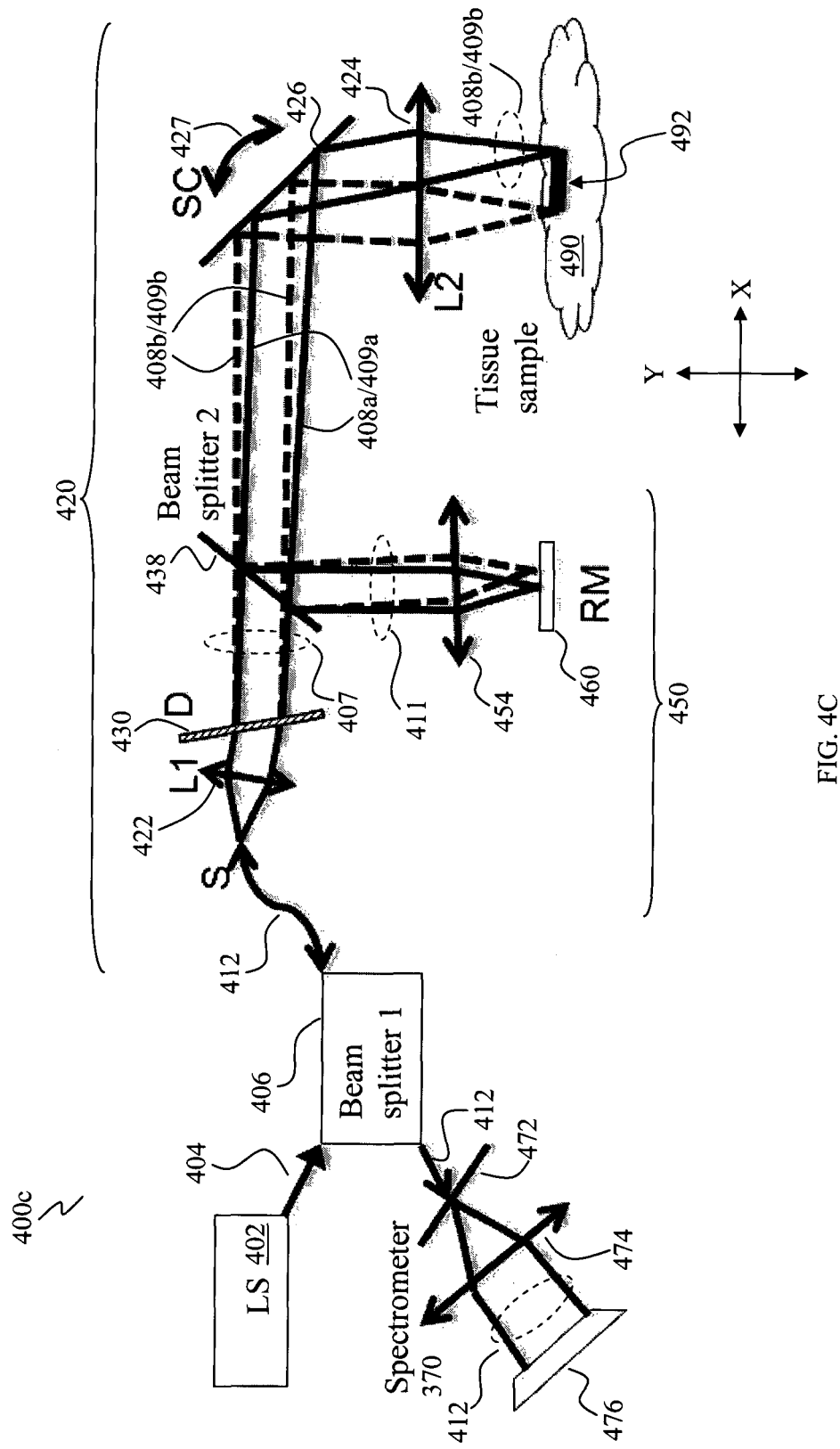
FIG. 4C shows a schematic view of an optical imaging device, according to various embodiments.

FIG. 4C shows a schematic view of an optical imaging device 400c, according to various embodiments. The optical imaging device 400c may be an extended-source SD-OCT device, for example a line-source SD-OCT device. The optical imaging device 400c may be similar to the optical imaging device 400b, for example in terms of optical elements, optical arrangement and operation, except that another beam splitter (beam splitter 2) 438 is included in the path of the extended-source illumination pattern 407, from which the reference arm 450 may be formed, rather than formed from the beam splitter 406. In this way, by adding a second beam splitter 438 after the dispersive element (D) 430, the dispersion between the sample arm 420 and the reference arm 450 may be at least substantially balanced.

As described above, the geometry of the source or the extended-source illumiation pattern 407 may be controlled or manipulated at the sample arm 420 of the optical imaging devices 400a, 400b, 400c.

In various embodiments, the source may be extended by a dispersive element 430 from a point source to a line source to provide a line illumination pattern, and the illumination pattern on the sample 490 is a line.

In various embodiments, by using the dispersive element 430 to generate an extended-source illumination pattern (e.g. line illumination pattern) 407, the return light signal 409a, 409b reflected by a given point of the sample 490 is encoded by a certain wavelength, so that at the detector (spectrometer 470), it may be possible to determine that a signal associated with a particular wavelength is from a particular point of the sample 490, rather than from any other points. By doing so, transverse resolution may be maintained for the line illumination pattern.

An extended-source illumination pattern may also be created by using a slit or a cylindrical lens, which may generate a line illumination pattern. However, there may be a degradation of transverse resolution along the direction of the line illumination generated by a slit or a cylindrical lens as, when collected using a single mode fiber, once inside the single mode fiber (integration over all the points), it is not possible to differentiate which photon is from which location in the line illumination.

The sample light radiation scanning method of various embodiments will now be described by way of the following non-limiting examples. At a given point O $(x_1, y_1, z_1)$ on a tissue sample that is illuminated by a sample light radiation, for small-source SD-OCT, the entire available wavelengths in the spectrum of the sample light radiation is directed, to point O at the same time hi contrast, in extended-source SD-OCT, at a given time point only a portion of the spectrum of the sample light radiation is directed to point O for a tissue sample, so that the irradiance at point O may be lower than that of small-source SD-OCT, and therefore safer.

Figure 6:
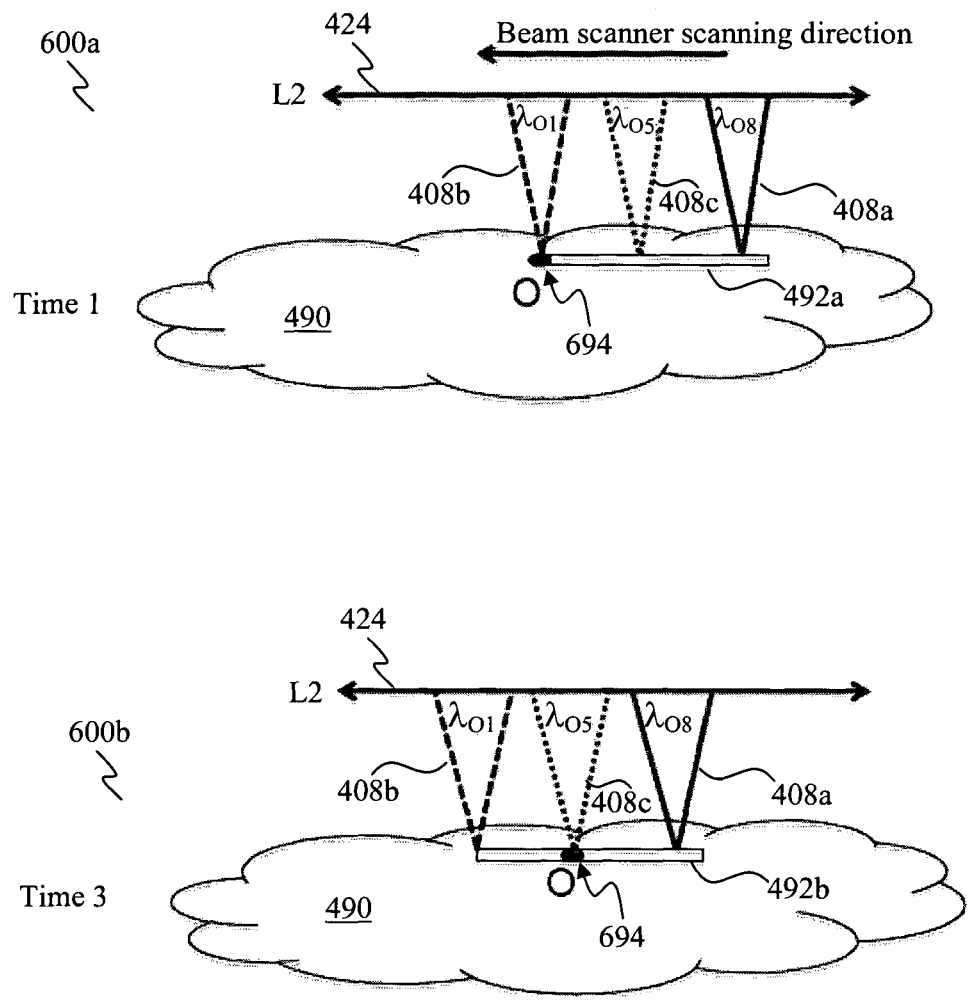
FIG. 6 shows, as schematic views, scanning of a sample at various scanning times of a sample light radiation scanning method, according to various embodiments.

FIG. 6 shows, as schematic views, scanning of a sample (e.g. tissue sample) 490 at various scanning times of a sample light radiation scanning method, according to various embodiments for extended source SD-OCT. As shown by the schematic diagram 600a, at Time 1, the sample light radiation (illumination pattern) may provide an extended-source illumination, for example a line illumination pattern 492a, on the sample 490, where different spectral bands of the sample light radiation may be directed to different parts or points on the line 492a on the sample 490. For clarity and ease of understanding, only three spectral bands 408a, 408b, 408c having lights with respective center wavelengths $\lambda_{O8}$, $\lambda_{O1}$, and $\lambda_{O5}$ of the sample light radiation are shown in FIG. 6. For example, spectral band light 408b having a center wavelength $\lambda_{O1}$ may be directed towards the sample 490 at point O, indicated by 694, to illuminate that portion of the sample 490 at Time 1. The beam scanner (SC) 426 may then be operated to scan the sample light radiation, thereby shifting the line illumination pattern 492a for scanning of the sample 490 at Time 2, Time 3, Time 4 and so on. Based on the beam scanner scanning direction indicated in FIG. 6, for example, as shown by the schematic diagram 600b, at Time 3, a line illumination pattern 492b may be directed onto the sample 490, where the line illumination pattern 492b is equivalent to the line illumination pattern 492a at Time 1 but shifted to the left. At Time 3, spectral band light 408c having a center wavelength $\lambda_{O5}$ may be directed towards the same point O 694. Therefore, in various embodiments for an extended-source SD-OCT device, the center wavelength, at a particular point of the sample 490, such as point O 694 ($\lambda_{O1, 2, 3 \ldots n}$, n=number of pixels of the line scan camera), sweeps as a function of time when the beam scanner (SC) 426 scans the sample light radiation along the direction of the linear source or line pattern 492a, 492b, as illustrated in FIG. 6. In this way, different spectral bands of the sample light radiation may illuminate a particular point or region of the sample 490 at different times.

For any given spectral band, since the spectral line width is small, the lateral spot size (or lateral resolution) may be diffraction limited.

The signal mapping method or spectral signal remapping method will now be described by way of the following non-limiting examples.

In an extended-source SD-OCT device, different spectral bands arrive, for example at point O (694, FIG. 6), as a function of time instead of simultaneously in the case of a small-source SD-OCT device. Therefore, spectral signal or information acquired by the detector (e.g. spectrometer 470, FIGS. 4A to 4C) for point O may need to be remapped in time domain so as to obtain the correct axial profile associated with the section of the sample corresponding to point O. With regard to point O, the exact arrival time of each wavelength associated with a respective spectral band may be calculated based on the parameters of the dispersive element D (e.g. 430, FIGS. 4A to 4C), the relay optics (e.g. L3 lens 432 and L4 lens 434, FIG. 4A), and the beam scanner (e.g. SC 426, FIGS. 4A to 4C) angular position. The spectral data acquired by the detector may be remapped according to the calculated arrival time of each wavelength to obtain the entire interference spectrum corresponding to point O of the sample.

Figure 7:
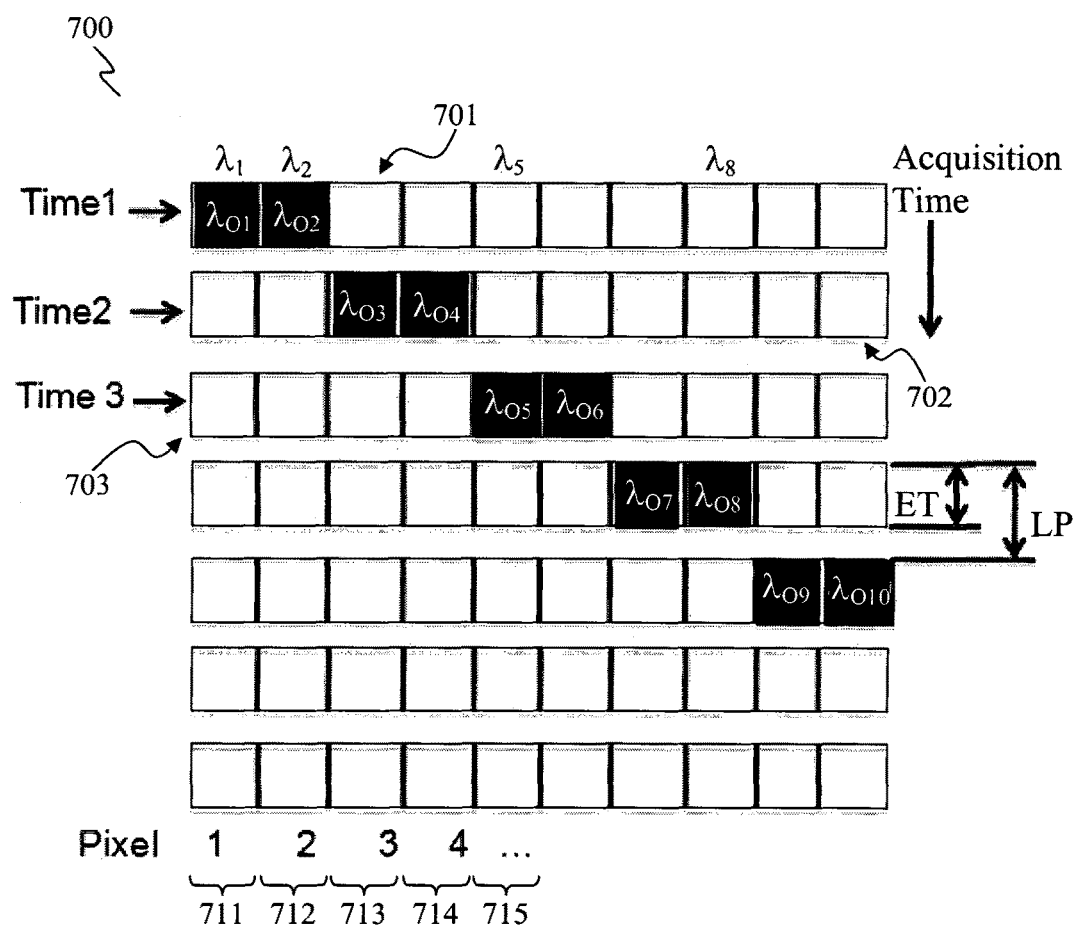
FIG. 7 shows a schematic representation of a spectral signal remapping algorithm, according to various embodiments.

FIG. 7 shows a schematic representation 700 of a spectral signal remapping algorithm, according to various embodiments. The representation 700 illustrates a method of nearest-point interpolation employed for remapping the spectral signal. In FIG. 7, the acronyms "ET" and "LP" refer to exposure time and camera acquisition line period respectively. The spectral data may be acquired as a function of time (e.g. Time 1, 2, 3 . . . ). Each horizontal array (e.g. 701, 702, 703) represents a spectrum acquired at a given time using the spectrometer. As examples, the horizontal array 701 represents a spectrum acquired at Time 1, the horizontal array 702 represents a spectrum acquired at Time 2, while the horizontal array 703 represents a spectrum acquired at Time 3. Each cell (e.g. 711, 712, 713, 714, 715) of a horizontal array 701, 702, 703 represents data from each pixel of the line camera of the spectrometer. The black cells in the horizontal arrays 701, 702, 703 represent the spectral data originating from point O.

Referring to FIGS. 6 and 7, at Time 1, the spectral band with the center wavelength $\lambda_{O1}$ is dwelling right at point O 694 of the sample 490 so as to illuminate point O 694, so that the first pixel of the spectral data acquired at Time 1 is the first pixel of the spectral data for point O 694. As shown in FIG. 6, At Time 1, spectral data, associated with the spectral band having a center wavelength $\lambda_{O1}$, originating from point O 694, may be provided on Pixel 1 711 of the camera of the detector. Further, for a spectral band having a center wavelength $\lambda_{O2}$, the calculated arrival time may be between two acquisitions at Time 1 and Time 2, and the spectral data corresponding to point O 694 may be obtained through interpolating adjacent spectral data, such as the spectral data associated with the center wavelength $\lambda_{O1}$, in time domain, and provided on Pixel 2 712. At the same time, spectral data originating from other points or sections of the sample may be provided on other pixels, e.g. Pixel 3 713. At Time 2, spectral data, associated with a spectral band having a center wavelength $\lambda_{O3}$, originating from point O may be provided on Pixel 3 713. Spectral data for a spectral band having a center wavelength $\lambda_{O4}$ corresponding to point O 694 may be obtained through interpolating the spectral data associated with the center wavelength $\lambda_{O3}$, in time domain, and provided on Pixel 4 714. At Time 3, spectral data, associated with a spectral band having a center wavelength $\lambda_{O5}$, originating from point O may be provided on Pixel 5 715. The obtained spectral data may then be interpolated to obtain data associated with a center wavelength $\lambda_{O6}$.

For point O 694, entire interference spectrum corresponding to point O 694 of the sample 490 may be extracted based on the algorithm described in the context of FIGS. 6 and 7, so that the axial profile at point O 694 may be obtained by Fourier transforming the extracted inferference spectrum after linearization in optical frequency space. As the optical signal of the entire spectrum of the light source originating from point O 694 is used to generate the axial line profile, the axial resolution is only limited by the coherence length of the light source.

As the optical signal of any given spectral band originating from point O 694 may be diffraction limited in the lateral direction, after Fourier transform, the lateral resolution may be diffraction limited.

Spectral remapping may be carried out using an image phantom with a straight line, such as based on a United States Air Force resolution standard. Results obtained using USAF (United States Air Force) 1951 resolution standard will now be described.

FIG. 8A shows a diagram illustrating a spectral remapping approach or method. The left diagram 800a illustrates a B-scan (brightness scan) frame obtained by extended-source scanning. The left diagram 800a shows different triangles occupying different parts of the spectrum. For example, the triangle 802 occupies a red portion of the spectrum, the triangle 804 occupies a yellow-green portion, while the triangle 806 occupies a blue portion. Cross-correlation may be carried out, resulting in the different triangles 802, 804, 806 being at least substantially aligned, as illustrated in the right diagram 800b, to form an image.

FIG. 8B shows a diagram 810 of the DC component of one B-scan frame of a resolution chart based on the resolution standard. The diagram 810 illustrates a spectral frame composed of 812 A-lines acquired in a B-mode scan, in which the horizontal axis is the time or number of A-line, and the vertical axis is the wavelength. The strips (some of which represented by 812, 814, 816, 818) represent the metal-coated high reflective pattern of the resolution standard. A spectral remapping vector may be obtained by performing cross-correlation analysis. The spectral frame illustrated in FIG. 8B after remapping is shown as diagram 820 in FIG. 8C.

Figure 9:
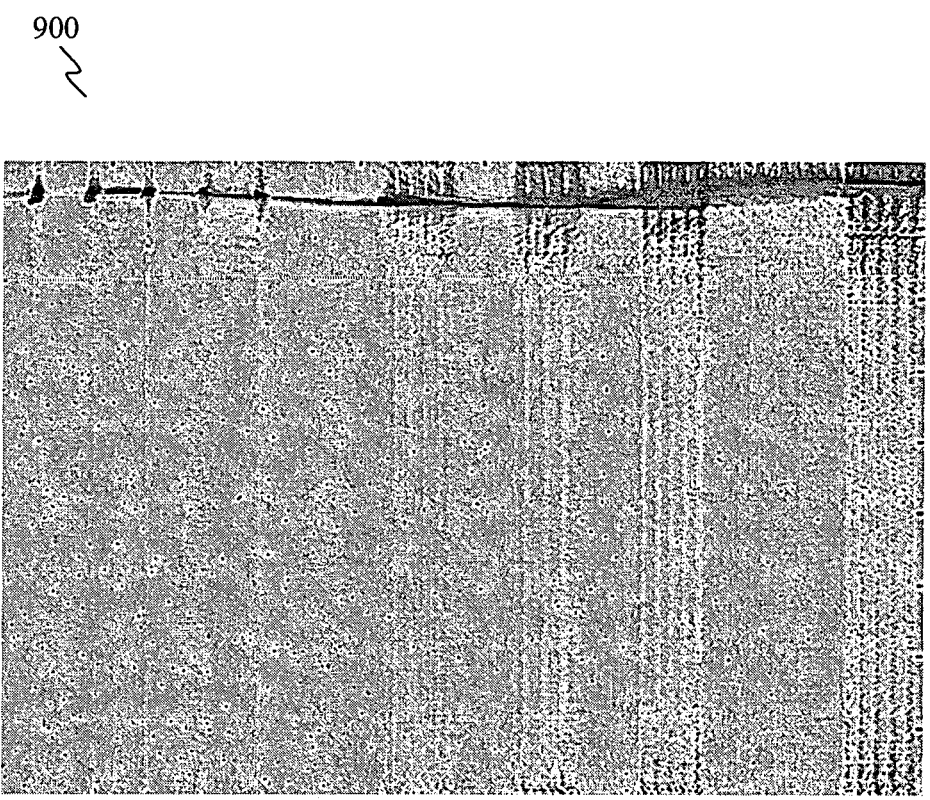
FIG. 9 shows a cross-sectional image of the resolution chart obtained by Fourier Transforming of the spectral remapped B-scan frame of FIG. 8C.

FIG. 9 shows a cross-sectional image 900 of the resolution chart obtained by Fourier Transforming of the spectral remapped B-scan frame of FIG. 8C. The cross-sectional image 900 shows a representative cross-sectional image of the USAF 1951 resolution target.

Various embodiments, including the device or system, may be commercialized after confirmatory safety validation. Although various embodiments conform to the safety standard set by ANSI Z136 in the United States and IEC 60825-1 internationally, confirmatory safety validation may be needed to obtain FDA (US Food and Drug Administration) approval.

Technically, as illustrated in FIGS. 4A to 4C, commercial applications of various embodiments may require minimal hardware and software modification to existing commercial products, so that in principle almost all the existing SD-OCT units may be directly modified without major reconstruction.

SD-OCT products have substantially or totally replaced TD-OCT products mainly because SD-OCT offers approximately 20-30 dB sensitivity advantage over TD-OCT. As described above, various embodiments may be capable of enhancing sensitivity of existing SD-OCT technology by more than approximately 10 dB. Therefore, the commercial potential of various embodiments may be enormous.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. An optical imaging device comprising:
   an optics arrangement comprising:
      a dispersive element configured to receive a first light and generate an extended-source illumination pattern comprising a plurality of separate spectral bands from the first light, the extended-source illumination pattern having a form which is elongated in a direction and the optics arrangement being configured to illuminate sections of a sample to be imaged with the plurality of separate spectral bands, and
      a scanning device configured to scan the extended-source illumination pattern across the sections of the sample at least along said direction such that each section of the sections of the sample is illuminated by each of the plurality of separate spectral bands as a function of time at respective time instances, wherein the optics arrangement is further configured to form an interference signal from a sample light comprising respective return lights from the sections of the sample, and a reference light; and
   a detector configured to receive the interference signal for generating an image corresponding to the sections of the sample, including, for each section of the sections of the sample, imaging said section based on information obtained from the interference signal corresponding to said each of the plurality of separate spectral bands that illuminated said section at said respective time instances.

2. The optical imaging device as claimed in claim 1, wherein the dispersive element comprises at least one of a prism and a grating.

3. The optical imaging device as claimed in claim 1, wherein the optics arrangement comprises a collimation lens configured to collimate the first light from which the extended-source illumination pattern is generated.

4. The optical imaging device as claimed in claim 1, wherein the optics arrangement comprises a beam splitter arranged to receive and split a light into the first light from which the extended-source illumination pattern is generated, and a second light from which the reference light is derived.

5. The optical imaging device as claimed in claim 1, wherein the optics arrangement comprises a relay optics assembly optically coupled to the extended-source illumination pattern.

6. The optical imaging device as claimed in claim 1, wherein the optics arrangement comprises a beam splitter arranged to receive and split light corresponding to the extended-source illumination pattern into a first portion for illuminating the respective sections of the sample, and a second portion from which the reference light is derived.

7. The optical imaging device as claimed in claim 1, wherein the optics arrangement comprises focusing optics for focusing the extended-source illumination pattern onto a focal plane on the sample corresponding to the sections of the sample.

8. The optical imaging device as claimed in claim 1, wherein the detector comprises a grating arranged to spectrally disperse the interference signal.

9. The optical imaging device as claimed in claim 1, further comprising a processor configured to obtain said information for each section of the sections of the sample from the interference signal for generating the image corresponding to the sections of the sample.

10. The optical imaging device as claimed in claim 9, wherein the processor is configured:
    to obtain, from the interference signal for each section of the sections of the sample, said information corresponding to said each of the plurality of separate spectral bands that illuminated said section at said respective time instances; and
    to interpolate the obtained information in time domain to obtain information corresponding to said section for a subsequent spectral band adjacent to a respective spectral band of the plurality of separate spectral bands.

11. The optical imaging device as claimed in claim 9, wherein the processor is configured to perform Fourier transform on the interference signal.

12. The optical imaging device as claimed in claim 1, further comprising a light source, wherein the optics arrangement is configured to generate the extended-source illumination pattern based on a light produced by the light source.

13. The optical imaging device as claimed in claim 1, wherein the extended-source illumination pattern is an oblong illumination pattern.

14. The optical imaging device as claimed in claim 1, wherein the extended-source illumination pattern is a line illumination pattern.

15. The optical imaging device as claimed in claim 1, wherein the extended-source illumination pattern has a length with a corresponding angular dimension that is more than 1.5 mrad.

16. A method for imaging a sample, the method comprising:
    generating, by a dispersive element, an extended-source illumination pattern comprising a plurality of separate spectral bands, from a first light received by the dispersive element, the extended-source illumination pattern having a form which is elongated in a direction;
    illuminating sections of a sample to be imaged with the plurality of separate spectral bands;
    scanning the extended-source illumination pattern across the sections of the sample at least along said direction such that each section of the sections of the sample is illuminated by each of the plurality of separate spectral bands as a function of time at respective time instances;
    forming an interference signal from a sample light comprising respective return lights from the sections of the sample, and a reference light; and
    generating an image corresponding to the sections of the sample based on the interference signal, including, for each section of the sections of the sample, imaging said section based on information obtained from the interference signal corresponding to said each of the plurality of separate spectral bands that illuminated said section at said respective time instances.

17. The method as claimed in claim 16, further comprising providing a collimated light, wherein generating an extended-source illumination pattern comprises generating the extended-source illumination pattern from the collimated light.

18. The method as claimed in claim 16, further comprising:
receiving a light; and
splitting the light into the first light from which the extended-source illumination pattern is generated, and a second light from which the reference light is derived.

19. The method as claimed in claim 16, further comprising focusing and collimating the plurality of separate spectral bands of the extended-source illumination pattern.

20. The method as claimed in claim 16, further comprising splitting light corresponding to the extended-source illumination pattern into a first portion for illuminating the respective sections of the sample, and a second portion from which the reference light is derived.

21. The method as claimed in claim 16, further comprising focusing the extended-source illumination pattern onto a focal plane on the sample corresponding to the sections of the sample.

22. The method as claimed in claim 16, further comprising spectrally dispersing the interference signal.

23. The method as claimed in claim 16, wherein generating an image comprises obtaining said information for each section of the sections of the sample from the interference signal.

24. The method as claimed in claim 23, wherein obtaining information comprises:
obtaining, from the interference signal for each section of the sections of the sample, said information corresponding to said each of the plurality of separate spectral bands that illuminated said section; and
interpolating the obtained information in time domain to obtain information corresponding to said section for a subsequent spectral band adjacent to a respective spectral band of the plurality of separate spectral bands.

25. The method as claimed in claim 23, wherein obtaining information comprises performing a Fourier transform on the interference signal.

26. The method as claimed in claim 16, wherein the extended-source illumination pattern is an oblong illumination pattern.

27. The method as claimed in claim 16, wherein the extended-source illumination pattern is a line illumination pattern.

28. The method as claimed in claim 16, wherein the extended-source illumination pattern has a length with a corresponding angular dimension that is more than 1.5 mrad.

29. A method for generating an image with diffraction limited lateral resolution and coherence length limited axial resolution using the optical imaging device as claimed in claim 1, the method comprising:
scanning an extended-source illumination pattern, having a form which is elongated in a direction, across an area of a sample at least along said direction such that each section of sections of the sample in the area to be imaged is illuminated by each of a plurality of separate spectral bands of an entire spectrum corresponding to the extended-source illumination pattern as a function of time at respective time instances; and
performing a spectral signal remapping algorithm to extract an entire interference spectrum corresponding to a section of the sections of the sample for generating an image corresponding to the area of the sample, wherein the entire interference spectrum is formed from return lights corresponding to the plurality of separate spectral bands that illuminated the section of the sample and a reference light at said respective time instances.

* * * * *